United States Patent [19]

Piccardi et al.

[11] 4,182,893

[45] Jan. 8, 1980

[54] ANTHELMINTIC BENZIMIDAZOL-CARBAMATES

[75] Inventors: Paolo Piccardi, Milan; Giovanni Confalonieri, Monza; Pier G. Ramella; Lino Da Col, both of Novara, all of Italy

[73] Assignee: Montedison S.p.A., Milan, Italy

[21] Appl. No.: 897,853

[22] Filed: Apr. 19, 1978

[30] Foreign Application Priority Data

Apr. 20, 1977 [IT] Italy .............................. 22645 A/77

[51] Int. Cl.² ................... A61K 31/415; C07D 235/32
[52] U.S. Cl. .................................. 424/273 B; 548/306

[58] Field of Search ................... 548/306; 424/273 R, 424/273 B

[56] References Cited

U.S. PATENT DOCUMENTS

| 3,929,821 | 12/1975 | Beard et al. | 548/306 |
| 3,929,823 | 12/1975 | Beard et al. | 548/306 |
| 3,929,824 | 12/1975 | Beard et al. | 548/306 |

Primary Examiner—Natalie Trousof

[57] ABSTRACT

Benzimidazol(2)methylcarbamates substituted in position 5(6) are disclosed, together with a method for preparing them, and use thereof in suitable form for combatting intestinal, pulmonary and hepatic parasites, particularly Helminthes, in animals.

3 Claims, No Drawings

ANTHELMINTIC BENZIMIDAZOL-CARBAMATES

THE PRIOR ART

The 5(6)-substituted benzamidazoles are described in the literature, as is the fact that they exhibit anthelmintic activity. See, for instance, German patent applications Nos. 2,029,637 and 2,164,690; French Pat. Nos. 1,556,824 and 2,052,988; and U.S. Pat. Nos. 3,010,968 and 3,915,986.

Some of the 5(6)-substituted benzamidazoles are available on the market, including the products marketed by Smith Kline Co. under the trademarks "Albenzadole", "Oxybendazole" and "Parbendazole"; the product marketed by Hoechst Co. under the trademark "Phenbendazole"; the "Oxfendazole" of Syntex Co., the products "Combendazole" and "Thiabendazole" of Merck-Sharp & Doehm; and the product "Mebendazole" of the Jassen Co.

THE PRESENT INVENTION

One object of this invention is to provide new benzimidazol-carbamates substituted in 5(6) position and which exhibit anthelmintic activity against gastrointestianl parasites. In particular, the benzimidazol-carbamates of the invention exhibit anthelmintic activity against Helminthes which is often superior to that of the known anthelmintics.

This and other objects are achieved by the invention which provides new benzimidazol-carbamates of the general formula (I):

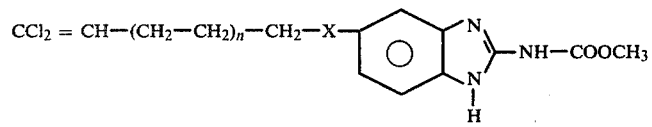

(I)

wherein:
X=S; SO
n=0; 1; 2.

The benzimidazol-carbamates of general formula (I), and in particular those wherein n=0 and 1, and X=S and SO, have shown an anthelmintic action against gastrointestinal Helminthes often superior to that of the known compounds. Moreover, they have shown an activity on pulmonary Helminthes that is nonexistent, or rare or weak in compounds in which the substituent in position 5(6) is an alkyl or phenyl group bound directly or through sulphur, oxygen or a CO group to the benzimidazole ring, as appears from Table I, infra.

The new benzimidazol-carbamates of our invention have been prepared by the following series of reactions, wherein R represents the $CCl_2=CH(CH_2-CH_2)_n-CH_2-$ groups:

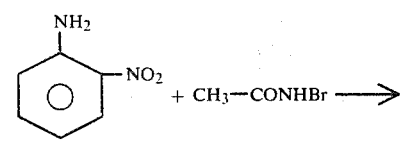

(1)

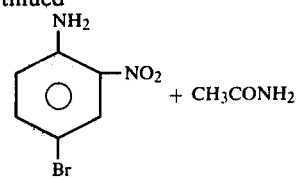

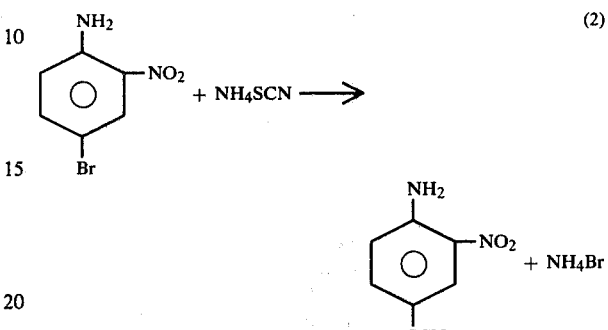

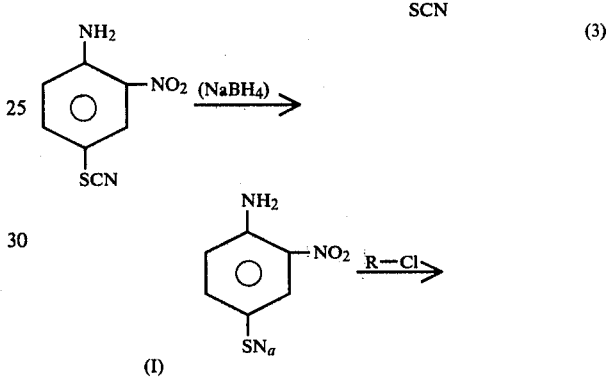

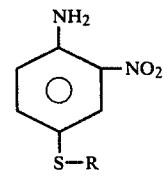

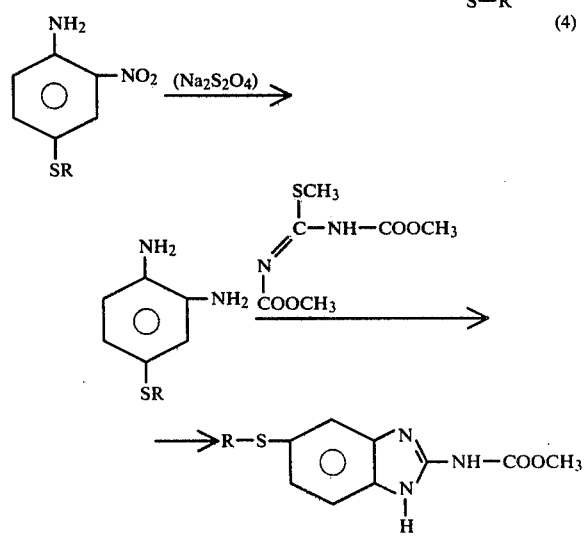

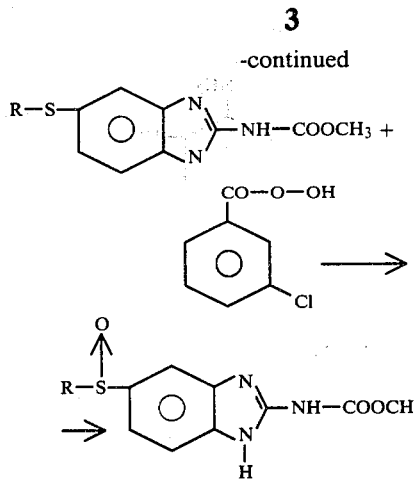

Reactions 1 and 2 may be conducted without isolating the p.bromo-o-nitroaniline that is formed. The reduction of the sulphocyanate of the o-nitroaniline with NaBH₄ leads directly to the alkaline salt of mercaptan which is directly reacted with the dichloro-alkylene halide. 4-dichloroalkylene-nitroaniline is reduced with sodium hydrosulphite to the corresponding phenylendiamine, and the latter is reacted with 1,3-bis-dimethoxycarbonyl-S-methyl-isothiourea to give the 5(6) substituted benzimidazol-carbamate which, by oxidation with m-chloroperbenzoic acid, gives its sulphoxide, as is indicated by reaction (5).

The anthelmintic infections sensitive to benzimidazolcarbamates in the main are the intestinal infections in breeding stocks of high economical importance. Most of the products act also on helmintic pulmonary and hepatic infections.

The most active compounds include:
the 5(6)-[(3,3-dichloroprop-2-en-1-yl)-thio] benzimidazol-2-methylcarbamate having the following characteristics:
m.p.=200°-202° C.—white solid;
elemental analysis, found: C=43.36%; H=3.32%; N=12.58%. theor: C=43.38%; N=3.34%; N=12.65%.
pure at thin-layer chromatographic analysis (t.l.x.).
the 5(6)-[3,3-dichloroprop-2-en-1-yl]sulphoxide of benzimidazol-2-methylcarbamate having the following characteristics:
m.p.=280° C. dec., pinkish-white solid pure at the t.l.c. analysis (absence of unoxidized precursor).

the 5(6)-[(5,5-dichloropent-4-en-1-yl)-thio-] benzimidazol-2-methylcarbamate having the following characteristics:
m.p.=183°-185° C., whitish solid;
elemental analysis, found: C=46.39%; H=4.24%; N=11.57%. theor: C=46.66%; H=4.22%; N=11.66%.
pure at t.l.c. analysis.
the 5(6)-[5,5-dichloropent-4-en-1-yl]sulphoxide of benzimidazol-2-methylcarbamate having the following characteristics:
m.p.=190° C., yellowish white solid, pure at t.l.c. analysis and free from unoxidized precursor.
the 5(6)-[(7,7-dichlorohept-6-en-1-yl)-thio]benzimidazol-2-methylcarbamate having the following characteristics:
m.p.=154° C., pinkish white solid;
elemental analysis, found: C=49.60%; H=4.70%; N=10.80%. theor: C=49.48%; H=4.89%; N=10.82%.
The NMR, IR and Mass spectra of all the above listed products are consistent with the structure.

The activity of the compounds has been studied in particular on sheep in the fight against gastroenteric Helminthes of the kind Ostertagia sp., Oesophagostomum sp., Trichostrolgylus sp. Some of the compounds (for instance those of numbers 2 and 3 of Table I) proved active against Plathyhelminthes of the Dyctiocaulus type.

The activity against the studied Helminthes varies considerably from compound to compound. Some, for instance, are active on *Fasciola hepatica*, others again on *Moniezia*.

The results of a series of tests undertaken on nematoda Helminthes and cestoda Helminthes of sheep and carried out with the products of this invention, in comparison with a series of currently used benzimidazole derivatives are summarized in Table I in which the data are expressed as percentage of reduction of infestation at the indicated doses. Aqueous suspensions of the drugs indicated in the Table were administered by mouth, in doses of 5 and 2.5 mg/kg to sheep infected with intestinal Helminthes (Osertagia sp., Oesophagostomum sp., Trichostrongylus sp.), pulmonary Helminthes (Dyctiocaulus sp.) and cestoda Helminthes (Moniezie).

The excrements were gathered for 48 hours after treatment and were examined both for Helminthes as well as for the reduction of layed eggs. Moreover, 48 hours after the treatment, the sheep were sacrificed (butchered) in order to evaluate the percentage of eliminated Helminthes.

TABLE I

Compounds of general formula:

| | | Ostertagia Oesophagostomum Trichostrongylus | | Dictocaulus | | Moniezia | | Fasciola Hepatica |
|---|---|---|---|---|---|---|---|---|
| No. | R = | 5 mg/kg | 2.5 mg/kg | 5 mg/kg | 2.5 mg/kg | 5 mg/kg | 2.5 mg/kg | 5 mg/kg |
| 1 | —S—CH₂—CH=CCl₂ | 100 | 100 | * | * | * | * | * |
| 2 | —SO—CH₂—CH=CCl₂ | 100 | 100 | 100 | 100 | 100 | * | 100 |
| 3 | —S—(CH₂)₃—CH=CCl₂ | 100 | 100 | 100 | 100 | 100 | * | 100 |
| 4 | —SO—(CH₂)₃—CH=CCl₂ | 100 | 100 | 50 | 20 | * | * | 50 |
| 5 | —S—(CH₂)₅—CH=CCl₂ | 100 | 80 | 100 | 80 | 100 | * | * |
| 6 | —SO—(CH₂)₅—CH=CCl₂ | 100 | 100 | 80 | 50 | 60 | 20 | 70 |

TABLE I-continued

Compounds of general formula: [benzimidazole-NH—COOCH₃ with R substituent]

| No. | R= | Ostertagia Oesophagostomum Trichostrongylus 5 mg/kg | Ostertagia Oesophagostomum Trichostrongylus 2.5 mg/kg | Dictocaulus 5 mg/kg | Dictocaulus 2.5 mg/kg | Moniezia 5 mg/kg | Moniezia 2.5 mg/kg | Fasciola Hepatica 5 mg/kg |
|---|---|---|---|---|---|---|---|---|
| Albendazole | —S—CH₂—CH₂—CH₂ | 80 | 20 | 60 | * | 70 | * | 50 |
| Oxibendazole | —O—CH₂—CH₂—CH₃ | active only at > doses | * | * | * | * | * | * |
| Phebendazole | —S—phenyl | 100 | 50 | 100 | 40 | 60 | * | active only at > doses |
| Oxfendazole | —SO—phenyl | 100 | 70 | 100 | 50 | 100 | 50 | 50 |
| Mebendazole | —CO—phenyl | active only at > doses | * | 50 | * | 80 | 20 | * |
| Cambendazole | (H₃C)₂CH—O—C(O)—NH— benzimidazole-thiazole | active only at > doses | * | 50 | * | 80 | 10 | * |
| Parbendazole | —CH₂—CH₂—CH₂—CH₃ | active only at > doses | * | * | * | 50 | * | * |
| Thiabendazole | benzimidazole-thiazole | active only at 50 mg/kg | * | 20 | * | * | * | * |

NOTE:
* = inactive.

The new products can be administered to animals by one of the usual veterinary methods for anthelmintic treatment, as by mouth in the form of boli, tablets, suspensions ("liquid drench"), powder, paste or parenterally in the form of an injectable liquid.

Low-weight animals are treated with doses of just a few milligrams, while animals of greater weight such as ruminants, sheep and horses, may require doses of around one gram per subject.

It is possible to administer single doses repeated 1–2 times a day, up to a maximum of 5 times a day, in order to attain a full disinfestation of the animals.

Practically, the active compound is usually formulated with a veterinary vehicle or is directly introduced into the fodder or feed. In this case the active compound may be either mixed with or dispersed in one of the fodder components in the form of swallowable capsules or tablets. The capsules may be made either of a rigid or a soft gelatin.

The vehicle may also be a diluent or a pharmaceutical excipient of the type usually used in the formulation of medicines. Suitable carriers which are readily available are, for instance: maize starch, lactose, saccharose, calcium phosphate, gelatin, stearic acid, magnesium stearate, dextrine, agar, pectines, "terra alba", etc.

The method of administering these active compounds may vary quite a lot and will depend on the specific requirements and, in particular, on the available equipment.

For the oral administration of the medicine, it is often useful to employ a liquid formulation that is either an emulsion, a suspension or a solution, either in water or in suitable organic liquids, for instance in peanut oil.

The following examples are given to illustrate the invention in more detail, and are not intended to be limiting.

EXAMPLE 1

Preparation of 4-[-(3,3-dichloroprop-2-en-1-yl)-thio]-2-nitroaniline

Under moderate stirring and at room temperature, there were mixed together 51.2 millimols of 2-nitro-4-thiocyano-aniline dissolved in 25 cc of dimethylformamide (DMF) with 54 millimols of sodium-borohydride dissolved in 25 cc of DMF. The temperature rose autogenously up to 30°–35° C. The mixture was kept under constant stirring for 1 hour at room temperature (15°–20° C.) after which there were introduced 66 millimols of 1,1,3-trichloropropene (1), regulating the feed so as to maintain the temperature below 25° C.

After the addition was completed, the mixture was heated at 100° C. for 3 hours. The reaction mass was then cooled down and poured into water under vigorous stirring. Thereupon, the reaction mass was extracted with chloroform; the organic extracts were gathered together, dried on $Na_2SO_4$ and the solvent was removed under vacuum. The yield in raw product thus obtained amounted to 85% and the product could be used directly for the successive synthesis. There was obtained a product showing a purity greater than 93% and the achieved overall yield amounted to 75% after a crystallization from $CH_3OH$ (m.p.=102° to 104° C.).

EXAMPLES 2 AND 3

By the same method as in Example 1, there were obtained the following derivatives:

4-[(5,5-dichloro-pent-4-en-1-yl)-thio]-2-nitroaniline, yield=80%.

4-[(7,7-dichloro-ept.-6-en-1-yl)-thio]-2-nitroaniline, yield=85%.

EXAMPLE 4

Preparation of 4[(3,3-dichloroprop-2-en-1-yl)-thio]-orthophenylendiamine

In 340 cc of a 1:1 (by volume) mixture of methanol-water containing 43 g of $Na_2S_2O_4$ were suspended 34.4 millimols of 4-[(3,3-dichloropropenyl)-thio]-2-nitroaniline. The reduction of the nitro-group was achieved in very short times (10–15 min.) as was ascertained by thin-layer chromatography. After the reduction was completed, the methanol and part of the water were removed under vacuum thereby obtaining an oily suspension which was then extracted with chloroform. The organic extracts, after drying on anhydrous $Na_2SO_4$, and evaporation of the solvent under vacuum, yielded, with practically quantitative yields, the raw diamine (an intensely colored thick oil) which was directly used for the successive stage.

EXAMPLE 5

Preparation of 5(6)-[(3,3-dichloroprop-2-en-1-yl)-thio]benzimidazol-2-methylcarbamate In 20 cc of an ethanol-water-acetic acid (40:40:1) mixture were dispersed 16 millimols of 4-[(3,3-dichloropropenyl)-thio]-o.phenyldiamine and 18 millimoles of methoxycarbonylmethylisothiourea. The reaction mixture was refluxed for 4 hours. Thereupon, the solid formed in the reaction medium was filtered and recrystallized from methanol and chloroform (1:1) thereby obtaining the desired benzimidazolcarbamate (yield=50%; m.p.=202°–204° C.). Greater yields are obtained in longer reaction times.

EXAMPLE 6

Preparation of 5-(6)-[(3,3-dichloroprop.-2-en-1-yl]-sulphoxide of benzimidazol-2-methyl-carbamate Into a mixture consisting of chloroform (400 cc), methanol (100 cc) and acetic acid (2 cc) were dissolved 2.39 millimols of the thioether obtained as described in Example 5.

The solution was cooled down to 0° C. and 2.51 millimols of m-chloroperbenzoic acid were added. After 1 hour, the reaction was completed, as could be verified by thin-layer chromatography [silica gel. eluent: a mixture of $CHCl_3$ (3), $CH_3COOC_2H_5$(2), $CH_3OH$(1)].

The organic solution thus obtained was washed with 150 cc of a saturated aqueous solution of $NaHCO_3$. The chloroform phase was then dried on $Na_2SO_4$ and the solvent was evaporated under vacuum.

Thereby was obtained an oily residue which, diluted with methanol, crystallized yielding the raw sulphoxide in quantitative yields. The crystallization of the raw product from methanol gave the pure product in yields of 85% (m.p.=280° C. dec.).

EXAMPLES 7–9

Operating as described in Examples 4 and 5, and starting from 5-(6)-[5,5-dichloro-pent-4-en-1-yl)-thio]-2-nitro-aniline or from 4-[(7,7-dichloro-ept-6-en-1-yl)-thio]-2-nitro-aniline, there were obtained, respectively, 5-(6)-[(5,5-dichloro-pent-(4)-en-(1)-yl-thio]-benzimidazol-2-methylcarbamate (m.p. 183°–185° C.) and 5(6)-[(7,7-dichloro-ept-6-en-1-yl)thio]-benzimidazole-2-methylcarbamate (m.p. 154° C.).

From these thio-compounds, by reaction with equimolar amounts of m.chloroperbenzoic acid, there were obtained the corresponding sulphoxides: 5(6)-[5,5-dichloro-pent-4-en-1-yl]sulphoxide of benzimidazol-2-methylcarbamate (m.p.=190° C.). 5(6)-[7,7-dichloro-hept-6-en-1-yl]-sulphoxide of benzimidazol-2-methyl-carbamate.

What is claimed is:

1. Benzimidazol-(2)-methylcarbamate substituted in 5(6) position by the radical $—S—(CH_2)_3—CH=CCl_2$ and having the formula:

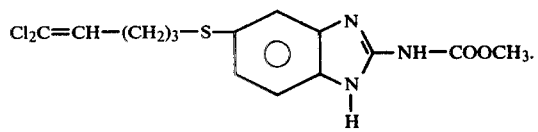

2. An anthelmintic composition comprising an ingestable carrier and, as the essential anthelmintic constituent of the composition, an effective amount of the benzimidazol-(2)-methylcarbamate of claim 1.

3. The method of combatting helmintic infections in animals which consists in administering to the animals an effective amount of an anthelmintic composition the essential anthelmintic constituent of which is the benzimidazol-(2)-methylcarbamate of claim 1.

* * * * *